(12) United States Patent
Chang et al.

(10) Patent No.: US 12,357,942 B2
(45) Date of Patent: Jul. 15, 2025

(54) HYBRID SYSTEM OF CARBON DIOXIDE COMPACT MEMBRANE SEPARATION AND CARBON RECYCLING FOR URBAN POWER PLANT FOR EFFLUENT CARBON DIOXIDE CONCENTRATION CONTROL

(71) Applicant: Korea District Heating Corp., Gyeonggi-do (KR)

(72) Inventors: Won Seok Chang, Gyeonggi-do (KR); Kyoung A Shin, Gyeonggi-do (KR); Jong Jun Lee, Gyeonggi-do (KR); Kyung Min Kim, Gyeonggi-do (KR); Hyeong Gyu Namgung, Gyeonggi-do (KR); Hyun Cheal Lee, Seoul (KR); Ji Hye Yu, Incheon (KR)

(73) Assignee: Korea District Heating Corp., Gyeonggi-do (KR)

( * ) Notice: Subject to any disclaimer, the term of this patent is extended or adjusted under 35 U.S.C. 154(b) by 690 days.

(21) Appl. No.: 17/833,925

(22) Filed: Jun. 7, 2022

(65) Prior Publication Data

US 2022/0387928 A1    Dec. 8, 2022

(30) Foreign Application Priority Data

Jun. 7, 2021  (KR) .................. 10-2021-0073579

(51) Int. Cl.
*B01D 53/22*    (2006.01)
*B01D 53/30*    (2006.01)
(Continued)

(52) U.S. Cl.
CPC ......... *B01D 53/229* (2013.01); *B01D 53/226* (2013.01); *B01D 53/30* (2013.01);
(Continued)

(58) Field of Classification Search
CPC .... B01D 53/229; B01D 53/226; B01D 53/30; B01D 53/346; B01D 53/84; C01F 11/18; C01F 5/24
(Continued)

(56) References Cited

U.S. PATENT DOCUMENTS

| 8,951,773 | B2 | 2/2015 | Kato | |
|---|---|---|---|---|
| 2013/0071889 | A1* | 3/2013 | Kato | ...................... C12P 7/649 |
| | | | | 435/134 |
| 2021/0053012 | A1 | 2/2021 | Chang et al. | |

FOREIGN PATENT DOCUMENTS

| JP | 04-126516 | 4/1992 |
|---|---|---|
| JP | 09-276648 | 10/1997 |

(Continued)

OTHER PUBLICATIONS

KR101927378B1 Machine English Translation (Year: 2018).*
(Continued)

*Primary Examiner* — Michael L Hobbs
*Assistant Examiner* — Lenora A Abel (57) ABSTRACT

Disclosed is a hybrid system of carbon dioxide compact separation membrane and carbon recycling for an urban power plant for effluent carbon dioxide concentration control, including a blower into which an exhaust gas is input and which distributes the exhaust gas, a photo-culture process unit which receives the exhaust gas from the blower, performs a photo-culture process using microalgae, and discharges a first treatment gas, a mixing tank into which the exhaust gas supplied from the blower and the first treatment gas are input, a separation membrane process unit which receives a second treatment gas mixed in the mixing tank, and separates a third enriched gas from the second treatment gas using a plurality of separation membranes, a mineralization reaction unit which mineralizes carbon dioxide using the third enriched gas separated in the separation membrane
(Continued)

process unit and discharges a third treatment gas to the mixing tank, a sensor unit which measures a carbon dioxide concentration discharged from each process using a plurality of sensors, and a control unit which controls operations of the photo-culture process unit, the separation membrane process unit and the mineralization reaction unit according to a carbon dioxide content of the inflow exhaust gas.

18 Claims, 5 Drawing Sheets

(51) Int. Cl.
  *B01D 53/34* (2006.01)
  *B01D 53/84* (2006.01)
  *C01F 5/24* (2006.01)
  *C01F 11/18* (2006.01)
(52) U.S. Cl.
  CPC ......... *B01D 53/346* (2013.01); *B01D 53/84* (2013.01); *C01F 5/24* (2013.01); *C01F 11/18* (2013.01)
(58) Field of Classification Search
  USPC .......................................... 435/292.1; 47/1.4
  See application file for complete search history.

(56) References Cited

FOREIGN PATENT DOCUMENTS

| | | |
|---|---|---|
| JP | 2003-227683 | 8/2003 |
| KR | 10-2011-0098620 | 9/2011 |
| KR | 10-1462411 | 11/2014 |
| KR | 10-1927378 | 12/2018 |
| KR | 101927378 B1 * | 12/2018 |
| KR | 10-2020-0129647 | 11/2020 |
| WO | WO 2019/172501 | 9/2019 |

OTHER PUBLICATIONS

Notice of Reasons for Refusal Dated May 23, 2023 From the Japan Patent Office Re. Application No. 2022-091784 and Its Translation Into English. (6 Pages).

Request for the Submission of an Opinion Dated Aug. 18, 2023 From the Korean Intellectual Property Office Re. Application No. 10-2021-0073579 and Its Translation Into English. (16 Pages).

* cited by examiner

HYBRID SYSTEM OF CARBON DIOXIDE COMPACT MEMBRANE SEPARATION AND CARBON RECYCLING FOR URBAN POWER PLANT FOR EFFLUENT CARBON DIOXIDE CONCENTRATION CONTROL

RELATED APPLICATION

This application claims the benefit of priority of Korea Patent Application No. 10-2021-0073579 filed on Jun. 7, 2021, the contents of which are incorporated by reference as if fully set forth herein in their entirety.

FIELD AND BACKGROUND OF THE INVENTION

The embodiment relates to a hybrid system of carbon dioxide compact separation membrane and carbon recycling for an urban power plant for effluent carbon dioxide concentration control. In more detail, the embodiment relates to a hybrid system of carbon dioxide compact separation membrane and carbon recycling which can control effluent carbon dioxide concentration by effectively capturing and separating carbon dioxide, and using it as a post-treatment to perform new carbon recycling that can be converted into various expensive substances, in an urban power plant in the city center or even in a small space of industrial complex, at a low cost. In particular, the embodiment relates to a system capable of effectively reducing carbon dioxide concentration in treated exhaust gas.

With industrial development, the problem of global warming has emerged due to the increase in atmospheric carbon dioxide concentration, and the biggest cause of the increase in atmospheric carbon dioxide concentration is the use of fossil fuels such as coal, oil and liquefied natural gas, which are used in the energy industry.

From the beginning of the $19^{th}$ century when industrialization began, green gas concentrations such as carbon dioxide ($CO_2$), methane ($CH_4$), nitrogen dioxide, and halocarbons have increased in the atmosphere, and have rapidly increased from the mid-$20^{th}$ century.

As global warming is accelerating due to the increase in greenhouse gases, emission and disposal of these gases are more strictly regulated. Since the UN Conference on environment and development held in Rio, Brazil in June 1992, international interest in global warming is gradually increasing, and an international consensus on greenhouse gas reduction was made, such that developed countries agreed in 2010 to reduce global greenhouse gas emissions by 52%, compared to 1990. Particularly, the treatment of $CO_2$ accounting for approximately 80% of greenhouse gases causing global warming has become a more important issue.

Various technologies such as $CO_2$ separation membrane capture technology, $CO_2$ mineralization technology, and photo-culture technology using microalgae are emerging to treat the emitted $CO_2$ component.

However, each technology has an advantage of treating $CO_2$, but also has various problems such as system installation costs, $CO_2$ throughput, and a low $CO_2$ reduction rate per unit area.

In order to solve this problem, a conventional art rapidly treats the exhaust gas of an urban power plant with a compact membrane separation process that can be installed even in narrow spaces, so that the carbon dioxide in an inflow exhaust gas can be collected/separated by 80 to 90% after the treatment, thereby lowering the carbon dioxide concentration in the treated gas to about 1%.

In particular, high-calcium powder is produced while treating carbon dioxide by 80% through the mineral carbonation process using an enriched flue gas, and this is treated with the microalgae process by using the enriched flue gas to produce expensive antioxidants with the photo-cultured microalgal biomass.

However, in order to dehydrate and dry the calcium powder or biomass produced in the process, a lot of energy is consumed. Therefore, there is a need for effective thermal energy.

In addition, in a hybrid process in which separation membrane, mineralization, and microalgae are sequentially linked, when the carbon dioxide concentration in the inflow exhaust gas rises to 5% or more, an effective operation method is required to maintain the treatment gas concentration to 1% or less.

SUMMARY OF THE INVENTION

An object of an embodiment is to effectively reduce carbon dioxide and secure economic feasibility by producing expensive substances using compact carbon dioxide collection and separation and carbon recycling technology through this, in a small space such as an urban power plant or industrial complex, at a low cost.

In addition, there is a need for an operation control system that can reduce the carbon dioxide concentration in an effluent gas through effective treatment according to the carbon dioxide concentration in the exhaust gas of an urban power plant, and an object of an embodiment is to derive an effective drying method of calcium carbonate and biomass drying process, which requires a lot of energy.

The problems to be solved by the present invention are not limited to the problems mentioned above, and other problems not mentioned here will be clearly understood by those of ordinary skilled in the art from the following description.

An embodiment of the present invention may include a blower into which an exhaust gas is input and which distributes the exhaust gas; a photo-culture process unit which receives the exhaust gas from the blower, performs a photo-culture process using microalgae, and discharges a first treatment gas; a mixing tank into which the exhaust gas supplied from the blower and the first treatment gas are input; a separation membrane process unit which receives a second treatment gas mixed in the mixing tank, and separates a third enriched gas from the second treatment gas using a plurality of separation membranes; a mineralization reaction unit which mineralizes carbon dioxide using the third enriched gas separated in the separation membrane process unit and discharges a third treatment gas to the mixing tank; a sensor unit which measures a carbon dioxide concentration discharged from each process using a plurality of sensors; and a control unit which controls operations of the photo-culture process unit, the separation membrane process unit and the mineralization reaction unit according to a carbon dioxide content of the inflow exhaust gas.

Preferably, the photo-culture process unit may include a drying unit which dries photo-cultured microalgae through a photo-culture process, the drying unit may dry the photo-cultured microalgae using a hot air of the hot exhaust gas and a pipe of district heating water.

Preferably, the drying unit may include a housing which is provided with an inlet and an outlet through which the microalgae are input, a drive belt which moves the microalgae input into the housing, the pipe of the district heating water which is disposed inside the drive belt, the hot air of the exhaust gas may be input into the housing.

Preferably, the pipe may be disposed in plurality at a lower portion of the drive belt.

Preferably, the pipe may be disposed in a zigzag at a lower portion of the drive belt.

Preferably, a roller mill may be disposed at a lower portion of the inlet of the housing.

Preferably, when the carbon dioxide content of the exhaust gas is higher than a preset concentration, the control unit may reduce an amount of the exhaust gas flowing to the photo-culture process unit and increase an amount of the exhaust gas flowing to the separation membrane process unit through the mixing tank.

Preferably, when the carbon dioxide content of the exhaust gas is higher than the preset concentration, the control unit may supply 90% or more of the inflow exhaust gas to the separation membrane process unit.

Preferably, the separation membrane process unit may receive the second treatment gas mixed in the mixing tank, and may separate the second treatment gas into a first enriched gas containing nitrogen, a second enriched gas containing oxygen and the third enriched gas containing carbon dioxide by using a plurality of separation membranes.

Preferably, the separation membrane process unit may separate the first enriched gas, the second enriched gas, and the third enriched gas using a first separation membrane, a second separation membrane, and a third separation membrane.

Preferably, the first enriched gas separated in the first separation membrane may move to the second separation membrane, the first enriched gas may be input and the second enriched gas may be separated in the second separation membrane, and the separated second enriched gas may move to the third separation membrane, the input second enriched gas may be separated to the third enriched gas in the third separation membrane.

Preferably, a membrane area ratio of the first separation membrane, the second separation membrane and the third separation membrane may decrease.

Preferably, the membrane area ratio of the first separation membrane, the second separation membrane and the third separation membrane may be 3:2:1.

Preferably, the separation membrane process unit may include a first circulation line that recirculates a gas that has passed through the first separation membrane, a second circulation line that recirculates a gas that has passed through the second separation membrane and a third circulation line that recirculates a gas that has passed through the third separation membrane, when the carbon dioxide content of the exhaust gas is determined to be higher than the preset concentration, the control unit may recirculate a gas that passes through the first separation membrane, the second separation membrane and the third separation membrane.

Preferably, a flow rate of the gas to be recirculated may be 0.3 times an inflow flow rate.

Preferably, the separation membrane process unit may further include an emergency separation membrane that is connected to the third enriched gas separated in the third separation membrane, when the carbon dioxide content of the exhaust gas is determined to be higher than the preset concentration, the control unit may control the third enriched gas to flow into the emergency separation membrane.

Preferably, the mineralization reaction unit may mineralize the carbon dioxide by reacting the third enriched gas with calcium hydroxide or calcium oxide.

Preferably, when the carbon dioxide content of the exhaust gas is determined to be higher than the preset concentration, the control unit may increase an amount of the calcium hydroxide or calcium oxide reacting with the third enriched gas.

According to an embodiment, even if the carbon dioxide concentration in an inflow exhaust gas of a power plant rises, it is possible to maintain the carbon dioxide concentration without additional facility supplementation through operation control technology such as control of an amount of the inflow exhaust gas, a change in a recirculation rate of gas separation membrane, and an increase in calcium amount input for mineralization.

In addition, there is an effect of obtaining an effective drying result of the produced calcium carbonate and biomass by using the hot air of the exhaust gas and the pipe heat of the heating supply water of a power plant.

Various and beneficial advantages and effects of the present invention are not limited to the above, and will be more easily understood in the course of describing specific embodiments of the present invention.

DESCRIPTION OF SPECIFIC EMBODIMENTS OF THE INVENTION

Hereinafter, preferred embodiments of the present invention will be described in detail with reference to the accompanying drawings.

However, the technical spirit of the present invention is not limited to some of the described embodiments, but may be implemented in various different forms, and as long as it is within the scope of the technical spirit of the present invention, one or more of the elements may be selectively combined and substituted between the embodiments.

In addition, terms (including technical and scientific terms) used in the embodiments of the present invention may be generally understood by those of ordinary skilled in the art to which the present invention belongs, unless specifically defined and described explicitly, and terms commonly used, such as terms defined in the dictionary, may be interpreted in consideration of the contextual meaning of the related art.

In addition, the terms used in the embodiments of the present invention are for describing the embodiments and are not intended to limit the present invention.

In this specification, a singular form may also include a plural form unless otherwise specified in a phrase, and when it is described as "at least one (or more than one) of A and (with) B, C", it may include one or more of all possible combinations of A, B, and C.

In addition, in describing the components of the embodiment of the present invention, terms such as first, second, A, B, (a), (b), etc. may be used.

These terms are only for distinguishing the component from other components, and are not limited to the essence, order, or sequence of the component by the terms.

In addition, when it is described that a component is 'connected', 'coupled' or 'contacted' to another component, it may include not only the case where the component is directly connected, coupled or contacted to the other component, but also the case where the component is 'connected', 'coupled' or 'contacted' to the other component by another component between the component and the other component.

In addition, when it is described as being formed or disposed on "upper (above) or lower (below)" of each component, the upper (above) or lower (below) includes not only the case where two components are in direct contact with each other, but also a case where one or more other components are formed or disposed between the two components. In addition, when expressed as "upper (above) or lower (below)", the meaning of not only the upper direction but also the lower direction based on one component may be included.

Hereinafter, an embodiment will be described in detail with reference to the accompanying drawings, but the same or corresponding components are given the same reference numerals regardless of reference numerals, and overlapping descriptions thereof will be omitted.

Since only key features have been clearly shown in FIGS. 1 to 5 in order to conceptually and clearly understand the present invention, various modifications of the illustrations are expected, and the scope of the present invention does not need to be limited by the specific shapes shown in the drawings.

Figure 1:
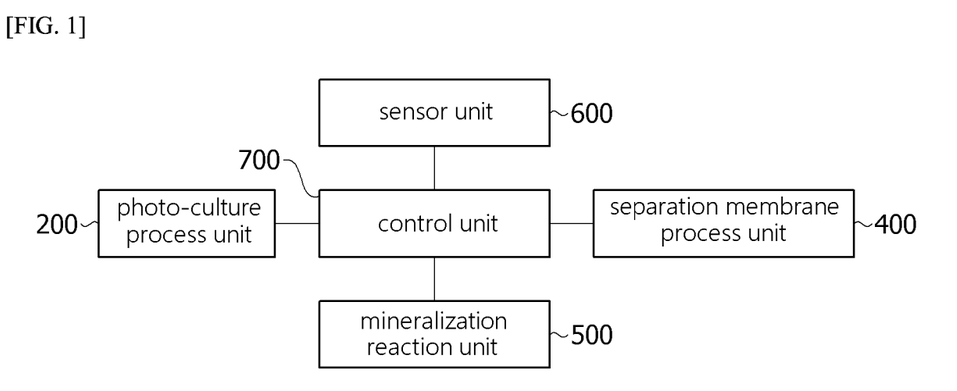
FIG. 1 is a block diagram of a hybrid system of carbon dioxide compact membrane separation and carbon recycling for an urban power plant for effluent carbon dioxide concentration control according to an embodiment of the present invention.
Figure 2:
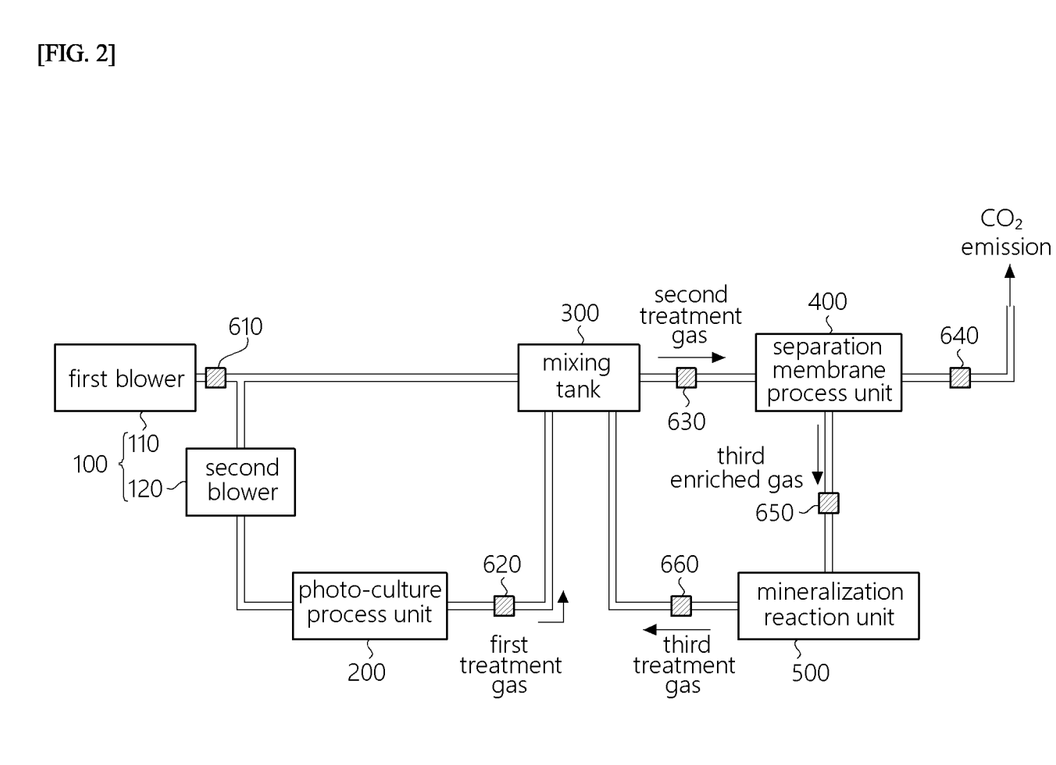
FIG. 2 is a structural diagram of the system of FIG. 1.
Figure 3:
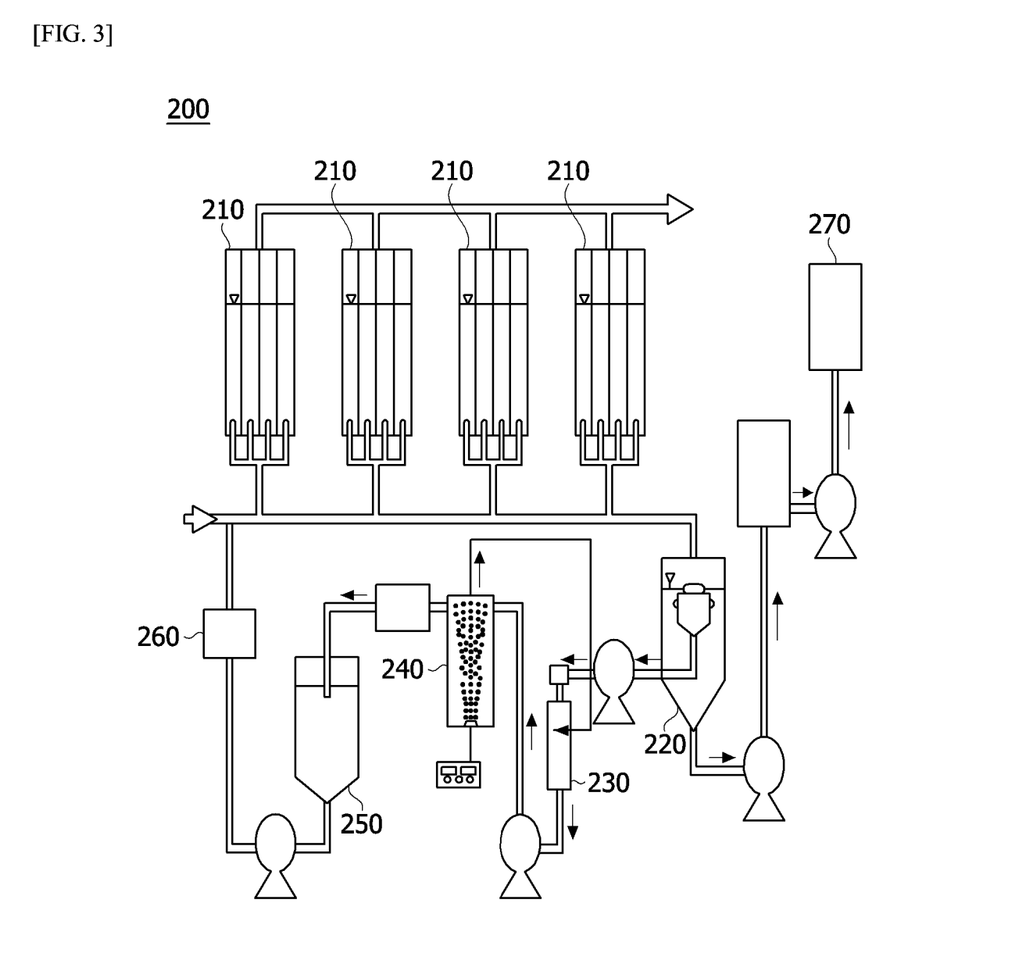
FIG. 3 is a structural diagram of a photo-culture process unit, which is a component of FIG. 1.
Figure 4:
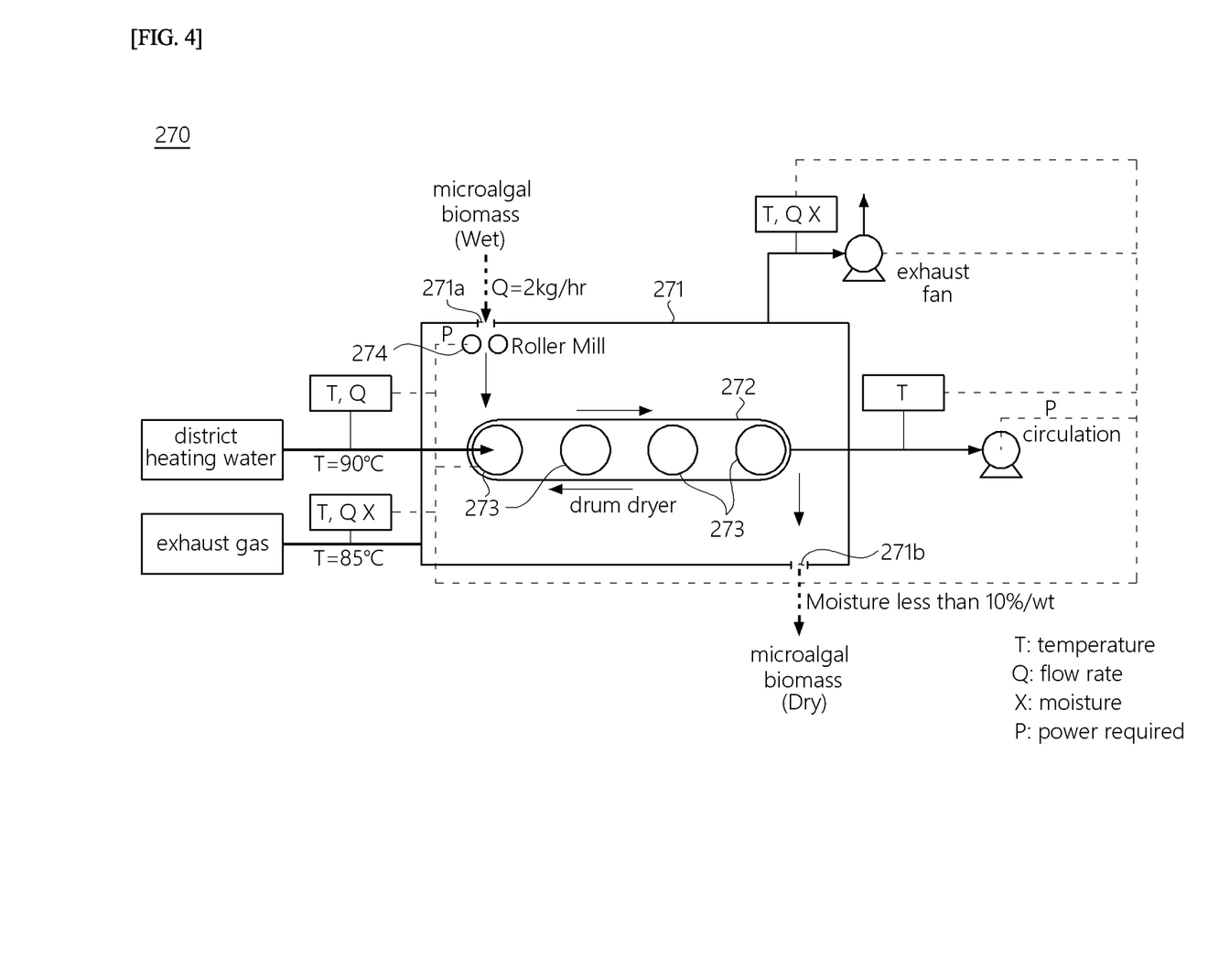
FIG. 4 is a diagram showing a structure of a drying unit, which is a component of FIG. 3.
Figure 5:
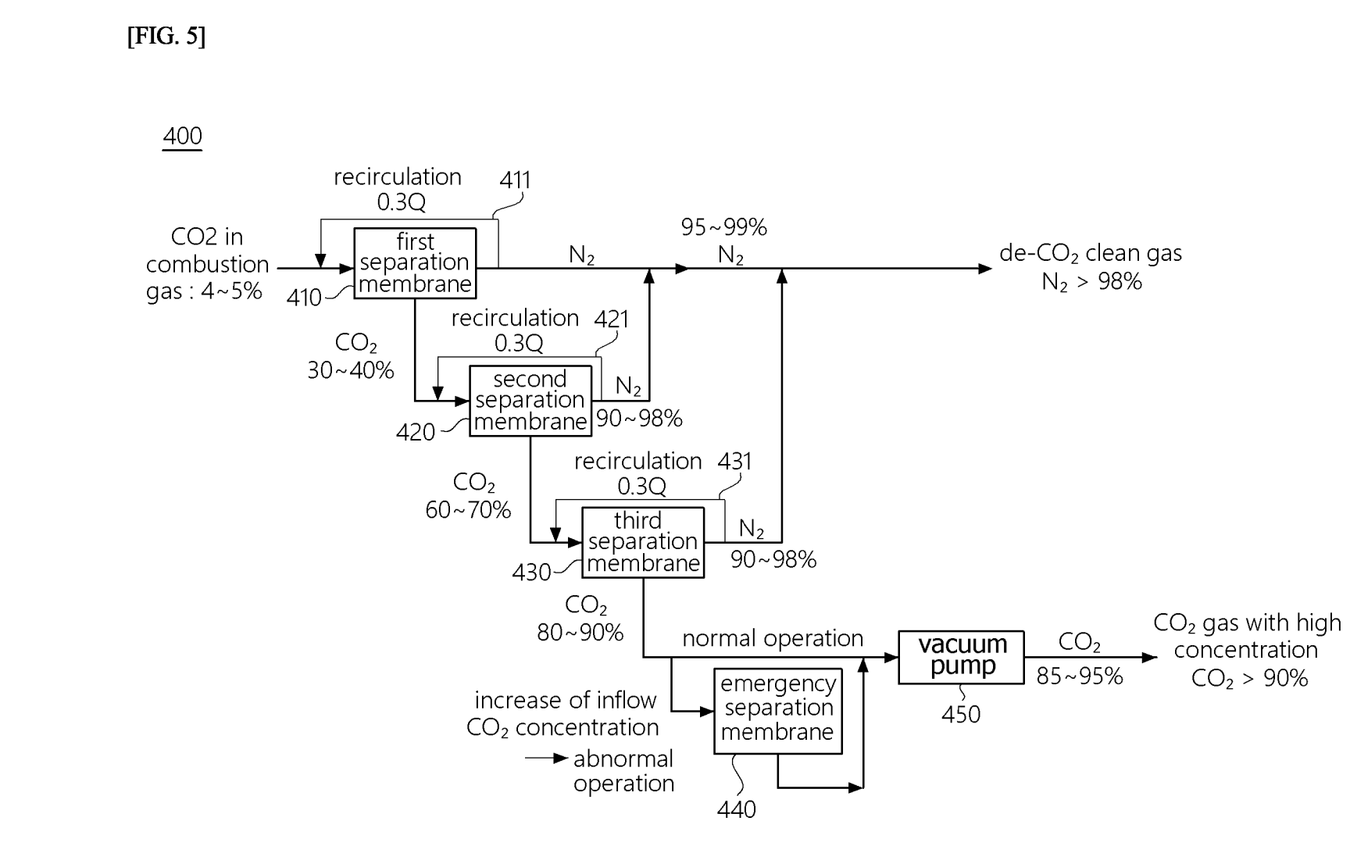
FIG. 5 is a diagram showing a structure of a separation membrane process unit, which is a component of FIG. 1.

FIG. 1 is a block diagram of a hybrid system of carbon dioxide compact membrane separation and carbon recycling for an urban power plant for effluent carbon dioxide concentration control according to an embodiment of the present invention, FIG. 2 is a structural diagram of the system of FIG. 1, FIG. 3 is a structural diagram of a photo-culture process unit, which is a component of FIG. 1, FIG. 4 is a diagram showing a structure of a drying unit, which is a component of FIG. 3, FIG. 5 is a diagram showing a structure of a separation membrane process unit, which is a component of FIG. 1.

Referring to FIGS. 1 to 5, a hybrid system of carbon dioxide compact separation membrane and carbon recycling for an urban power plant for effluent carbon dioxide concentration control according to an embodiment of the present invention may include a blower 100 into which an exhaust gas is input and which distributes the exhaust gas, a photo-culture process unit 200 which receives the exhaust gas from the blower 100, performs a photo-culture process using microalgae, and discharges a first treatment gas, a mixing tank 300 into which the exhaust gas supplied from the blower 100 and the first treatment gas are input, a separation membrane process unit 400 which receives a second treatment gas mixed in the mixing tank 300, and separates a third enriched gas from the second treatment gas using a plurality of separation membranes, a mineralization reaction unit 500 which mineralizes carbon dioxide using the third enriched gas separated in the separation membrane process unit 400 and discharges a third treatment gas to the mixing tank 300, a sensor unit 600 which measures a carbon dioxide concentration discharged from each process using a plurality of sensors, and a control unit 700 which controls operations of the photo-culture process unit 200, the separation membrane process unit 400 and the mineralization reaction unit 500 according to a carbon dioxide content of the inflow exhaust gas.

The exhaust gas containing carbon dioxide is input into the blower 100, and the blower 100 can distribute the exhaust gas to each component. In one embodiment, the blower 100 may include a first blower 110 to determine an inflow amount of the exhaust gas and a second blower 120 to control an amount of the exhaust gas input into the photo-culture process unit 200 among the exhaust gas inputted through the first blower 110.

In this case, the amount of exhaust gas inputted through the first blower 110 and the second blower 120 may be controlled through the control unit 700.

The photo-culture process unit 200 may receive the exhaust gas from the blower 100, perform photo-culture fixation using microalgae, and discharge the first treatment gas.

The photo-culture process unit 200 may perform a process of fixing the carbon dioxide using microalgae. Microalgae, which are phytoplankton, use sunlight as an energy source, and grow through photosynthesis for fixing the carbon dioxide.

The carbon dioxide fixation using these microalgae may use solar energy as a main energy source as in the case in which a plant photosynthesizes the carbon dioxide, and thus, there is an advantage that the energy consumption required to fix the carbon dioxide is very small.

Microalgae have a higher growth rate than plants, have a biomass productivity per unit area that is 20 to 100-fold higher than the first-generation biofuels such as soybean, corn and rapeseed, are able to be mass-cultured in salt water or wasteland, and are able to utilize various water resources such as sewage and seawater waste. Particularly, they have the advantage of being able to directly utilize the carbon dioxide component in the combustion exhaust gas from carbon emission sources such as a thermal power plant or LNG power plant for cell culture, and it is known that microalgae can photosynthesize more than 20 times the amount of conventional photosynthesis of pine trees through sunlight and carbon dioxide.

The microalgae process can convert carbon dioxide to various higher value-added substances such as biodiesel, a biopolymer, a medicine, health food and a natural pigment, and has an advantage that it is possible to develop an eco-friendly process with a low cost and economic feasibility due to no additional energy input by using solar light.

The microalgae that can be used for photo-culture may include, *Nechloris* sp., *Chlorella* sp., *Chlorococcum* sp., *Spirulina* sp., *Haematococcus* sp., *N eospongiococcum* sp., *Scenedesmus* sp., *Dunaliella* sp., and the like, but the present invention is not limited thereto. Generally, any microalgae having an ability to convert carbon dioxide to biomass can be used without limitation.

As shown in FIG. 3, the photo-culture process unit 200 may include a reactor 210, a recovery tank 220, a filter 230, an ozone reaction tank 240, an ultraviolet sterilization unit, a sterilized water storage tank 250, and a culture solution preparation unit 260 and a drying unit 270.

The reactor 210 is provided in plurality, and can grow photo organisms using a culture solution and carbon dioxide. A plurality of reactors 210 may be connected in parallel, and the carbon dioxide flowing into the reactor 210 and the culture solution may be mixed to grow photo organisms.

In this case, the carbon dioxide contained in the flue gas discharged from industrial facilities may be used, and various types of reactors 210 may be applied.

The recovery tank 220 may separate and discharge the culture solution in which the growth of the photo organisms is completed from the reactor 210 into the grown photo organisms and a waste culture solution. In one embodiment, the recovery tank 220 may collect and store the culture solution in which the growth has been completed in the reactor 210, and separate the grown photo organisms and the waste culture solution by a specific gravity difference to discharge each of them. In one embodiment, the recovery tank 220 may be formed to have an inclination so that the photo organisms can be collected when settling down, and it may be provided with a floating skimmer to discharge only the filtered supernatant water separated by specific gravity of the waste culture solution. The shape of the floating skimmer is not limited and may be provided in various shapes.

The photo-organisms discharged from the recovery tank 220 are introduced into a centrifuge, and the centrifuge can centrifuge the photo-organisms to remove moisture and discharge them.

The filter 230 may remove foreign substances and the photo-organisms from the waste culture solution discharged from the recovery tank 220. In this case, a disk filter 230 that can be reused through washing may be used as the filter 230.

The ozone reaction tank 240 may sterilize the waste culture solution passing through the filter 230 with ozone. The shape of the ozone reaction tank 240 is not limited, and may be transformed into various shapes advantageous for sterilization of the incoming waste culture solution.

In this case, the exhaust ozone of the ozone reaction tank 240 may be supplied to the filter 230 to backwash the filter 230. When the filter 230 is used for a long time, clogging of the filter 230 occurs. In the present invention, the filter 230 can be washed by circulating the exhaust ozone to prevent this problem.

The exhaust ozone of the ozone reaction tank 240 may be supplied to the filter 230 to regenerate the filter 230 through microbial sterilization and cleaning of the filter 230.

A pressure sensor may be disposed on a line through which the waste culture solution is supplied from the recovery tank 220 to the filter 230, and an exhaust ozone supply line in which a pressure higher than a preset pressure is detected by the pressure sensor may operate to wash the filter 230. In one embodiment, when a pressure of 1 bar or more is sensed by the pressure sensor, it may be set such that the exhaust ozone is circulated.

The ultraviolet sterilization unit may additionally sterilize the waste culture solution that has passed through the ozone reaction tank 240. The ultraviolet sterilization unit is disposed on a line moving from the ozone reaction tank 240 to the sterilized water storage tank 250, thereby preventing contamination of the sterilized water by secondary sterilization. In one embodiment, the ultraviolet sterilization unit may be arranged in the same longitudinal direction as the line to increase the sterilization time.

In the sterilized water storage tank 250, the waste culture solution that has passed through the ozone reaction tank 240 or the ultraviolet sterilization unit may be stored as sterilized water. In this way, the separated waste culture solution can be recycled as clean sterilized water through sterilization treatment of the ozone reaction tank 240 and the ultraviolet sterilization unit, and the clogging problem of the filter 230 is solved through backwashing using the exhaust ozone. Accordingly, additional costs for wastewater treatment and raw water production can be reduced.

The culture solution preparation unit 260 may include a medium tank, a stock solution supply unit, an acid-base supply unit, and a washing solution supply unit. The medium tank may prepare a culture solution by mixing the sterile water supplied from the sterile water storage tank 250, the stock solution supplied from the stock solution supply unit, and the acid or base supplied from the acid-base supply unit. The prepared culture solution may be initially supplied to the reactor 210 to regenerate the culture solution. Through this, a conventional medium tank may be provided with a stirrer for mixing the materials of the culture solution, and a pH meter for measuring the pH of the mixed solution inside may be disposed.

In addition, after the preparation of the culture solution is completed, a sprayer for washing the inside of the medium tank may be provided. The shape of the sprayer is not limited, and the sprayer may be provided in various shapes to facilitate cleaning.

A plurality of the stock solution supply units may be disposed, and the stock solution stored in each stock solution supply unit may contain different materials. The acid-base supply unit may introduce an acid or a base into the medium tank to adjust the pH measured from the pH meter to a preset value.

The washing solution supply unit may supply the washing solution to the inside of the medium tank when cleaning is required inside the medium tank. In one embodiment, 70% ethanol may be used as the washing solution.

The drying unit 270 may dry the photo-cultured microalgae through the photo-culture process in the form of biomass from which moisture has been removed to some extent through the recovery tank 220 and the centrifuge. The drying unit 270 may dry the photo-cultured microalgae using the hot air of the hot exhaust gas and the heat from the pipe 273 of the district heating water.

The drying unit 270 may include a housing 271, a drive belt 272, and a pipe 273.

The housing 271 provides a space for drying the photo-cultured microalgae through the photo-culture process. A plurality of pipes 273 is connected to the housing 271, and a pipe 273 of district heating water supplied from the outside may pass through, and the hot air of the hot exhaust gas may be input into the housing 271.

An inlet 271a for introducing microalgae may be disposed at an upper portion of the housing 271, and an outlet 271b for discharging the dried microalgae may be disposed at a lower portion of the housing 271.

A roller mill 274 is installed at the lower portion of the inlet 271a of the housing 271 to crush the microalgae.

The drive belt 272 is disposed inside the housing 271 to be circulated. The drive belt 272 may have a spirally rotating structure, and it may be provided with the structure in which the microalgae flowing in through the inlet 271a are seated at one end, and the microalgae that has been dried flows out through the outlet 271b at the other end.

The pipe 273 may be disposed inside the drive belt 272 to supply heat to the drive belt 272. The district heating water inputted through the pipe 273 transfers a high-temperature heat source to the microalgae. In one embodiment, the pipe 273 may be disposed in plurality under the drive belt 272 or may have a zigzag structure to increase the heat transferred from the lower portion of the drive belt 272.

The district heating water flowing in through the pipe 273 may be controlled with respect to temperature and flow rate and supplied to the inside of the housing 271, and the exhaust gas supplied to the housing 271 may be controlled with respect to temperature, flow rate and moisture and supplied to the inside of the housing 271.

In order to increase the drying efficiency of the drying unit 270, experiments were conducted in various ways.

The experiment was performed under the following conditions.

Conditions: 50 kg of biomass before drying (80% moisture content), 10 kg of biomass after drying (10% moisture content)

TABLE 1

| Drying method | Drying time (condition satisfied) |
|---|---|
| exhaust gas | 250 minutes |
| district heating water | 330 minutes |
| exhaust gas + district heating water | 145 minutes |
| exhaust gas + recovery water of district heating | 220 minutes |
| exhaust gas + water of low pressure boiler | 200 minutes |
| exhaust gas + steam turbine extract gas | 190 minutes |

As shown in Table 1, it took 250 minutes to satisfy the above conditions when drying only with an exhaust gas, it took 330 minutes to satisfy the above conditions when drying with district heating water, it took 145 minutes to satisfy the above conditions when dying with the association of the exhaust gas and the district heating water, it took 220 minutes to satisfy the above conditions when drying with the association of the exhaust gas and the recovery water of district heating, it took 200 minutes to satisfy the above conditions when drying with the association of the exhaust gas and the water of low pressure boiler, and it took 190 minutes to satisfy the above conditions when drying with the association of the exhaust gas and a steam turbine extract gas. As such, in order to increase the biomass drying efficiency, it was confirmed that the association of the exhaust gas and the district heating water has the highest efficiency. The exhaust gas supplied through the first blower 110 and the first treatment gas may be input into the mixing tank 300. In this case, the control unit 700 may control the carbon dioxide concentration of the mixed gas supplied to the separation membrane process unit 400.

The separation membrane process unit 400 may receive the second treatment gas mixed in the mixing tank 300, and separate the second treatment gas into a first enriched gas containing nitrogen, a second enriched gas containing oxygen and a third enriched gas containing carbon dioxide by using a plurality of separation membranes.

When the second treatment gas flows and passes through the plurality of separation membranes, the separation membrane process unit 400 may separate the second treatment gas into the enriched gas containing each component of nitrogen, oxygen, and carbon dioxide as a main component due to the separation pore difference and permeation rate of each component.

The separation membrane process unit 400 may separate the first enriched gas, the second enriched gas, and the third enriched gas using a first separation membrane 410, a second separation membrane 420, and a third separation membrane 430.

In one embodiment, in the separation membrane process unit 400, the second treatment gas inputted from the mixing tank 300 is input into the first separation membrane 410, the first enriched gas separated in the first separation membrane 410 moves to the second separation membrane 420, the second enriched gas separated in the second separation membrane 420 moves to the third separation membrane 430 and is extracted as the third enriched gas. The extracted enriched gas is enriched with the carbon dioxide of high concentration, and then, discharged.

The gas separated from the first separation membrane 410, the second separation membrane 420 and the third separation membrane 430 satisfies the carbon dioxide emission condition and may be discharged to the atmosphere.

A membrane area ratio of the first separation membrane 410, the second separation membrane 420 and the third separation membrane 430 used in the separation membrane process may decrease.

Table 2 below shows the test results of an enrichment rate and a recovery rate according to a membrane area ratio. The separation membrane used in the experiment of Table 2 was made of a polymer material of polysulfone.

TABLE 2

| Membrane area ratio of first separation membrane 410: second separation membrane 420: third separation membrane 430 | Enrichment rate (%) | Recovery rate (%) |
|---|---|---|
| 3:2:1 | 85 | 91 |
| 2:2:1 | 80 | 84 |
| 1:2:1 | 83 | 87 |
| 1:2:2 | 78 | 82 |
| 1:1:1 | 75 | 78 |

Referring to Table 2, when the membrane area ratio of the first separation membrane 410, the second separation membrane 420 and the third separation membrane 430 is 3:2:1, the best result was shown in the enrichment and recovery rates. In addition, the separation membrane process unit 400 may include a first circulation line 411 for recirculating the gas that has passed through the first separation membrane 410, a second circulation line 421 for recirculating the gas that has passed through the second separation membrane 420 and a third circulation line 431 for recirculating the gas that has passed through the third separation membrane 430. The circulation line disposed in the separation membrane process unit 400 may operate under the control of the control unit 700.

When the carbon dioxide content of the inflow exhaust gas is determined to be higher than a preset concentration, the control unit 700 may recirculate the gas passing through the first separation membrane 410, the second separation membrane 420 and the third separation membrane 430.

In general, when the carbon dioxide concentration in the inflow exhaust gas is constantly introduced as 4 to 5%, the carbon dioxide concentration in the final effluent gas is maintained at 1% or less. However, when the carbon dioxide concentration of the inflow exhaust gas rises to 7 to 9%, the carbon dioxide concentration in the final effluent exhaust gas increases to 2 to 3%.

Therefore, when the carbon dioxide concentration in the inflow exhaust gas is determined to be higher than a preset concentration, the control unit 700 may reduce the carbon dioxide concentration in the final effluent exhaust gas by recirculating the gas that has passed through the separation membrane using the circulation line.

In one embodiment, when the amount circulated through the circulation line is operated at a circulation rate of about 0.3 times the inflow flow rate, it was confirmed that the carbon dioxide concentration in the final effluent exhaust gas was reduced by 0.6 to 0.85%.

In addition, the separation membrane process unit 400 may further include an emergency separation membrane 440 through which the third enriched gas separated from the third separation membrane 430 can move. When the carbon dioxide content of the inflow exhaust gas is determined to be higher than a preset concentration, the control unit 700 may control the third enriched gas to flow into the emergency separation membrane 440.

The emergency separation membrane 440 may be connected in parallel to the first separation membrane 410, and may process 0.5 times the exhaust gas of the first separation membrane 410.

The mineralization reaction unit 500 may mineralize carbon dioxide by using the third enriched gas separated in the separation membrane process unit 400 and discharge the third treatment gas to the mixing tank 300.

The mineralization reaction unit 500 is a technology for synthesizing a new mineral by reacting the captured carbon dioxide with natural minerals or inorganic industrial waste discharged from industries.

The mineralization reaction unit 500 may permanently solidify the carbon dioxide by producing $CaCO_3$, $MgCO_3$ and carbonate through a mineralization reaction of the carbon dioxide in the exhaust gas with Ca and Mg components in the construction by-products (slag, waste concrete).

The carbonate produced is stable and does not dissolve well in water, it is not harmful to the environment because carbon dioxide cannot be released into the atmosphere, and the problem of carbon dioxide emission can be solved by permanently storing the carbon dioxide.

In this case, the first enriched gas containing high-purity nitrogen gas is microbubbled through a fine disperser and introduced into the mineralization reaction unit 500, and reacts with the third enriched gas supplied to the mineralization reaction unit 500. Thus, the inside of the mineralization slurry tank can be uniformly mixed.

In one embodiment, the mineralization reaction unit 500 may mineralize carbon dioxide by reacting the third enriched gas with calcium hydroxide or calcium oxide.

When the carbon dioxide concentration of the inflow exhaust gas is determined to be higher than a preset concentration, the control unit 700 may increase an amount of calcium hydroxide or calcium oxide reacting with the third enriched gas. In one embodiment, when the carbon dioxide concentration of the inflow exhaust gas rises to 7 to 9%, an amount of calcium hydroxide can be increased up to three times. When the inflow of calcium hydroxide is maximally introduced, the existing treatment rate of mineralized carbon dioxide increases from 70 to 80% to 87 to 99%, and as a result, it was confirmed that the final effluent carbon dioxide concentration was reduced by 0.4 to 0.7%.

The sensor unit 600 may measure the concentration of carbon dioxide emitted from each process using a plurality of sensors. The sensor unit 600 measures the concentration of carbon dioxide contained in the inflow exhaust gas, and when the carbon dioxide concentration is determined to be higher than a preset concentration based on this, the sensor unit 600 transmits a signal to the control unit 700, and the control unit 700 may perform the above-mentioned process based on this signal.

In one embodiment, the sensor unit 600 may include a first sensor 610 that measures carbon dioxide in the exhaust gas flowing into through the first blower 110, and a second sensor 620 that measures the carbon dioxide of the first treatment gas discharged from the photo-culture process unit 200, a third sensor 630 that measures the carbon dioxide of the mixed gas discharged from the mixing tank 300, a fourth sensor 640 that measures the carbon dioxide discharged from the separation membrane process unit 400, a fifth sensor 650 that measures the carbon dioxide of the third enriched gas discharged from the separation membrane process unit 400 and a sixth sensor 660 that measures the carbon dioxide discharged from the mineralization reaction unit 500.

The control unit 700 may control the operations of the photo-culture process unit 200, the separation membrane process unit 400 and the mineralization reaction unit 500 according to the carbon dioxide content of the inflow exhaust gas.

The control unit 700 may control the flow rate of the gas supplied to and discharged from the blower 100, the photo-culture process unit 200, the mixing tank 300, the separation membrane process unit 400 and the mineralization reaction unit 500 by using the detection value of the sensor unit 600.

An object of the present invention is to control exhaust gas emission by controlling the concentration (%) of carbon dioxide finally discharged.

However, since an amount of inflow carbon dioxide or an amount of carbon dioxide to be treated is not always constant and the treatment efficiency is different, there is a problem in that an amount of carbon dioxide that is finally discharged varies.

In order to solve this problem in the present invention, when the carbon dioxide concentration sensed by the fourth sensor 640 is higher than a preset value, the carbon dioxide emission can be adjusted by controlling the components of the system.

When the carbon dioxide concentration detected by the fourth sensor 640 is higher than the preset value, the control unit 700 reduces an amount of exhaust gas flowing into through the first blower 110, increase an amount of exhaust gas flowing into the photo-culture process unit 200 through the second blower 120, and reduces the carbon dioxide concentration in the mixing tank 300, thereby controlling an amount of carbon dioxide finally discharged.

The control unit 700 may control the carbon dioxide concentration sensed by the fourth sensor 640 by increasing the recirculation rate of the separation membrane process unit 400, and control the carbon dioxide concentration sensed by the fourth sensor 640 by increasing an amount of calcium carbonate input to the mineralization reaction unit 500.

When the carbon dioxide content of the exhaust gas is determined to be higher than a preset concentration, the control unit 700 may reduce an amount of exhaust flowing to the photo-culture process unit 200, and increase an amount of the exhaust gas passing through the mixing tank 300 and then flowing to the separation membrane process unit 400.

In one embodiment, when the carbon dioxide content of the exhaust gas is determined to be higher than a preset concentration, the control unit 700 may supply 90% or more of the inflow exhaust gas to the separation membrane processing unit 400.

As described above, in the present invention, it is possible to increase the efficiency of the components used in the conventional hybrid system of carbon dioxide compact separation membrane and carbon recycling for an urban power plant for controlling the effluent carbon dioxide concentration. In particular, it is possible to control an amount of carbon dioxide finally discharged by increasing an amount of carbon dioxide captured and treated for each process when the carbon dioxide content in the inflow exhaust gas is high.

As described above, the embodiments of the present invention have been described in detail with reference to the accompanying drawings.

The above description is merely illustrative of the technical spirit of the present invention, and those of ordinary skilled in the art to which the present invention pertains may make various modifications, changes and substitutions within the scope without departing from the essential characteristics of the present invention. Accordingly, the embodiments disclosed in the present invention and the accompanying drawings are for explaining, not limiting, the technical spirit of the present invention, and the scope of the technical spirit of the present invention is not limited by these embodiments and the accompanying drawings. The protection scope of the present invention should be construed by the following claims, and all technical spirits within the scope equivalent thereto should be construed as being included in the scope of the present invention.

REFERENCES

100: blower
110: first blower
120: second blower
200: photo-culture process unit
210: reactor
220: recovery tank
230: filter
240: ozone reaction tank
250: sterilized water storage tank
260: culture solution preparation unit
270: drying unit
271: housing
271a: inlet
271b: outlet
272: drive belt
273: pipe
274: roller mill
300: mixing tank
400: separation membrane process unit
410: first separation membrane
420: second separation membrane
411: first circulation line
421: second circulation line
440: emergency separation membrane
430: third separation membrane
431: third circulation line
450: vacuum pump
500: mineralization reaction unit
600: sensor unit
610: first sensor
620: second sensor
630: third sensor
640: fourth sensor
650: fifth sensor
660: sixth sensor
700: control unit

What is claimed is:

1. A hybrid system of carbon dioxide compact separation membrane and carbon recycling for an urban power plant for effluent carbon dioxide concentration control, comprising:
   a blower into which an exhaust gas is input and which distributes the exhaust gas;
   a photo-culture process unit which receives the exhaust gas from the blower, performs a photo-culture process using microalgae, and discharges a first treatment gas;
   a mixing tank into which the exhaust gas supplied from the blower and the first treatment gas are input;
   a separation membrane process unit which receives a second treatment gas mixed in the mixing tank, and separates a third enriched gas from the second treatment gas using a plurality of separation membranes;
   a mineralization reaction unit which mineralizes carbon dioxide using the third enriched gas separated in the separation membrane process unit and discharges a third treatment gas to the mixing tank;
   a sensor unit which measures a carbon dioxide concentration discharged from each process using a plurality of sensors; and
   a control unit which controls operations of the photo-culture process unit, the separation membrane process unit and the mineralization reaction unit according to a carbon dioxide content of the inflow exhaust gas.

2. The hybrid system according to claim 1, wherein the photo-culture process unit includes a drying unit which dries photo-cultured microalgae through a photo-culture process,
   the drying unit dries the photo-cultured microalgae using a hot air of the hot exhaust gas and a pipe of district heating water.

3. The hybrid system according to claim 2, wherein the drying unit includes:
   a housing which is provided with an inlet and an outlet through which the microalgae are input;
   a drive belt which moves the microalgae input into the housing;
   the pipe of the district heating water which is disposed inside the drive belt,
   the hot air of the exhaust gas is input into the housing.

4. The hybrid system according to claim 3, wherein the pipe is disposed in plurality at a lower portion of the drive belt.

5. The hybrid system according to claim 3, wherein the pipe is disposed in a zigzag at a lower portion of the drive belt.

6. The hybrid system according to claim 3, wherein a roller mill is disposed at a lower portion of the inlet of the housing.

7. The hybrid system according to claim 1, wherein when the carbon dioxide content of the exhaust gas is higher than a preset concentration, the control unit reduces an amount of the exhaust gas flowing to the photo-culture process unit, and increases an amount of the exhaust gas flowing to the separation membrane process unit through the mixing tank.

8. The hybrid system according to claim 7, wherein when the carbon dioxide content of the exhaust gas is higher than the preset concentration, the control unit supplies 90% or more of the inflow exhaust gas to the separation membrane process unit.

9. The hybrid system according to claim 7, wherein the separation membrane process unit receives the second treatment gas mixed in the mixing tank, and separates the second treatment gas into a first enriched gas containing nitrogen, a second enriched gas containing oxygen and the third enriched gas containing carbon dioxide by using a plurality of separation membranes.

10. The hybrid system according to claim 9, wherein the separation membrane process unit separates the first enriched gas, the second enriched gas, and the third enriched gas using a first separation membrane, a second separation membrane, and a third separation membrane.

11. The hybrid system according to claim 10, wherein the first enriched gas separated in the first separation membrane moves to the second separation membrane,
   the first enriched gas is input and the second enriched gas is separated in the second separation membrane, and the separated second enriched gas moves to the third separation membrane,
   the input second enriched gas is separated to the third enriched gas in the third separation membrane.

12. The hybrid system according to claim 11, wherein a membrane area ratio of the first separation membrane, the second separation membrane and the third separation membrane decreases.

13. The hybrid system according to claim 12, wherein the membrane area ratio of the first separation membrane, the second separation membrane and the third separation membrane is 3:2:1.

14. The hybrid system according to claim 11, wherein the separation membrane process unit includes a first circulation line that recirculates a gas that has passed through the first separation membrane, a second circulation line that recirculates a gas that has passed through the second separation membrane and a third circulation line that recirculates a gas that has passed through the third separation membrane,
when the carbon dioxide content of the exhaust gas is determined to be higher than the preset concentration, the control unit recirculates a gas that passes through the first separation membrane, the second separation membrane and the third separation membrane.

15. The hybrid system according to claim 14, wherein a flow rate of the gas to be recirculated is 0.3 times an inflow flow rate.

16. The hybrid system according to claim 14, wherein the separation membrane process unit further includes an emergency separation membrane that is connected to the third enriched gas separated in the third separation membrane,
when the carbon dioxide content of the exhaust gas is determined to be higher than the preset concentration, the control unit controls the third enriched gas to flow into the emergency separation membrane.

17. The hybrid system according to claim 1, wherein the mineralization reaction unit mineralizes the carbon dioxide by reacting the third enriched gas with calcium hydroxide or calcium oxide.

18. The hybrid system according to claim 17, wherein when the carbon dioxide content of the exhaust gas is determined to be higher than the preset concentration, the control unit increases an amount of the calcium hydroxide or calcium oxide reacting with the third enriched gas.

* * * * *